(12) United States Patent
Park et al.

(10) Patent No.: US 8,932,612 B2
(45) Date of Patent: Jan. 13, 2015

(54) COMPOSITION FOR COSMETIC RAW MATERIAL CONTAINING CELLULOSE DYED WITH NATURAL COLORING MATTER HAVING IMPROVED PHOTOSTABILITY, AND VISUAL CARRIER SYSTEM COMPRISING THE SAME

(75) Inventors: Byung-Ho Park, Chungbuk (KR); Ik-Joo Lee, Chungbuk (KR); Mi-Hyun Jang, Chungbuk (KR); Jae-Uk Lee, Chungbuk (KR)

(73) Assignee: KPT Ltd., Chungbuk (KR)

( * ) Notice: Subject to any disclaimer, the term of this patent is extended or adjusted under 35 U.S.C. 154(b) by 500 days.

(21) Appl. No.: 12/812,164

(22) PCT Filed: Oct. 17, 2008

(86) PCT No.: PCT/KR2008/006158
§ 371 (c)(1),
(2), (4) Date: Jul. 8, 2010

(87) PCT Pub. No.: WO2010/024496
PCT Pub. Date: Mar. 4, 2010

(65) Prior Publication Data
US 2010/0278888 A1 Nov. 4, 2010

(30) Foreign Application Priority Data
Aug. 25, 2008 (KR) .................. 10-2008-0082985

(51) Int. Cl.
*A61K 8/97* (2006.01)
*A61K 8/02* (2006.01)
*A61Q 1/02* (2006.01)
*B29B 9/00* (2006.01)
*A61K 8/19* (2006.01)
*A61K 8/26* (2006.01)
*A61K 8/27* (2006.01)
*A61K 8/73* (2006.01)

(52) U.S. Cl.
CPC ... *A61K 8/19* (2013.01); *A61K 8/26* (2013.01); *A61K 8/27* (2013.01); *A61K 8/731* (2013.01); *A61K 8/97* (2013.01); *A61K 8/0287* (2013.01); *A61K 2800/412* (2013.01); *A61K 2800/43* (2013.01); *A61K 2800/56* (2013.01)
USPC .................................. 424/401; 514/781; 264/8

(58) Field of Classification Search
None
See application file for complete search history.

(56) References Cited

U.S. PATENT DOCUMENTS

| 4,336,244 | A | * | 6/1982 | Woznicki et al. ............ 424/480 |
| 4,918,099 | A | * | 4/1990 | Moon ........................... 514/453 |
| 5,244,469 | A | * | 9/1993 | Shimoyama et al. ............. 8/438 |
| 5,750,379 | A | * | 5/1998 | Onodera et al. ................. 435/72 |
| 6,217,904 | B1 | * | 4/2001 | Midha et al. ................... 424/468 |
| 6,656,229 | B1 | * | 12/2003 | Taguchi et al. ..................... 8/405 |
| 2005/0287278 | A1 | * | 12/2005 | Quan et al. ..................... 426/597 |

FOREIGN PATENT DOCUMENTS

| JP | 09-03786 | 1/1997 |
| JP | 2008-050312 | 3/2008 |
| KR | 10-1994-02793 | 4/1994 |

* cited by examiner

*Primary Examiner* — Mina Haghighatian
*Assistant Examiner* — Luke Karpinski
(74) *Attorney, Agent, or Firm* — The PL Law Group, PLLC (57) ABSTRACT

The present invention relates to a composition for cosmetic raw material containing cellulose dyed with a natural coloring matter having improved photostability, and a visual carrier system comprising the same. In the composition for cosmetic raw material and the visual carrier system comprising the same according to the present invention, by using no iron oxide chemical coloring matter and applying a typical and natural dyeing method of cloths to the microcrystalline cellulose that is the cosmetic raw material, photostability that is a problem of the natural coloring matter in the related art is largely improved.

17 Claims, 6 Drawing Sheets

COMPOSITION FOR COSMETIC RAW MATERIAL CONTAINING CELLULOSE DYED WITH NATURAL COLORING MATTER HAVING IMPROVED PHOTOSTABILITY, AND VISUAL CARRIER SYSTEM COMPRISING THE SAME

TECHNICAL FIELD

The present invention relates to a composition for cosmetic raw material containing cellulose dyed with a natural coloring matter having improved photostability, and a visual carrier system comprising the same.

BACKGROUND ART

A visual carrier system that is used in cosmetics is the general term for raw materials that are used to seek an aesthetic effect by a visual property and stabilization of bioactive material simultaneously. However, mostly, the system is used only for the purpose of an aesthetic property, thus a visual carrier system having various colors is typically used.

In order to apply the visual carrier system to cosmetics, it is required that when the system is used for products, it has a predetermined form, when it is used, it is easily dissolved by shear stress to disappear on the skin, and a pellet has a marketable shape. In respects to the shape of the pellet, the marketability is provided by using a pelletization technology. The pelletization technology is a process technology for producing circular or semicircular particles having the fluidity that are called as pellets from very small powder or granule particles (Isaac Ghebre-Sellassie, Pharmaceutical Pelletization Technology, Marcel dekker, Inc., New York and Basel., pp 2-3 (1989)]. The pelletization technology may be classified into an agitation process, a compaction process, a layering process and a globulation process according to the production method, and the agitation process includes balling, the compaction process includes compaction and extrusion/spheronization, the layering process includes powderization and solutionization/suspensionization, and a globulation process includes spray drying and spray freezing.

As a visual carrier system that is produced by using the pelletization technology, there are unisphere manufactured by Induchem, Co., Ltd. in Switzerland and cosmophere manufactured by Pelletech, Co., Ltd., and unisphere and cosmophere are produced by using extrusion and spheronization processes by means of an excipient such as cellulose and lactose. In addition, a cellulose framework visual carrier system manufactured by Spheretech, Co., Ltd. is produced by using the extrusion and spheronization processes. A visual carrier system manufactured by Floratech, Co., Ltd, in the US is produced by using spray freezing of the globulation process, but has a disadvantage in that its use is limited to material such as wax which is present in a solid form at normal temperature and the particle size distribution is wide during the production (U.S. Pat. Nos. 6,432,421 B1, 6,280,746 B1). The pelletization technology of FLORATECH occupies a portion of the market, but has a relative limit in the type of material and production efficiency as compared to the visual carrier system of the cellulose framework.

In addition, in the most visual carrier systems use an iron oxide chemical coloring matter in order to show a color. However, water pollution occurs during the dyeing due to the chemical coloring matter and the chemical coloring meter may cause skin problems.

Accordingly, many studies have been made of a method for producing a cosmetic raw material using a natural coloring matter while a chemical coloring matter is not used. However, in the case of when the natural coloring matter powder extracted from the plant is used as the cosmetic raw material without processing, there is a problem in that since it is rapidly discolored by light, photostability is reduced.

Therefore, there is a need to develop a cosmetic raw material using the natural coloring matter having improved photostability.

DISCLOSURE OF INVENTION

Technical Problem

The present inventors have studied to develop a method for improving photostability of the cosmetic raw material using a natural coloring matter while an iron oxide chemical coloring matter is not used, produced a composition for cosmetic raw material that is dyed by applying a typical and natural dyeing method for clothes to microcrystalline cellulose that is a cosmetic raw material and a visual carrier system comprising the same, and found that the photostability of the composition for cosmetic raw material is largely improved, thereby accomplishing the present invention.

Technical Solution

It is an objection of the present invention to provide a composition for cosmetic raw material containing cellulose dyed with a natural coloring matter having improved photostability, and a visual carrier system comprising the same.

BEST MODE FOR CARRYING OUT THE INVENTION

The present invention provides a composition for cosmetic raw material containing cellulose dyed with a natural coloring matter that comprises 0.1 to 99.0 parts by weight of micro-crystalline cellulose, 0.10 to 20.0 parts by weight of a vegetable dyeing material, and 0.01 to 10.0 parts by weight of a mordant, and has a particle size in the range of 0.001 to 30 µm.

In addition, the present invention provides a visual carrier system that comprises a composition for cosmetic raw material containing cellulose dyed with a natural coloring matter and has a particle size of 20 to 30 meshes.

Hereinafter, a detailed description of the present invention will be given.

In the composition for cosmetic raw material that contains the cellulose dyed with the natural coloring matter according to the present invention, the iron oxide chemical coloring matter is not used and a typical and natural dyeing method of cloths is applied to the microcrystalline cellulose that is the cosmetic raw material.

The microcrystalline cellulose may be selected from a microcrystalline cellulose which is registered in the cosmetic raw material or a dried powder obtained by extracting a vegetable dyeing material that mostly contains cellulose as a constitution material.

The vegetable dyeing material comprises a natural coloring matter, and comprises one or more that are selected from the group consisting of a green tea, a *Caesalpiniae Lignum*, a tumeric, a safflower, a gromwell and a indigo plant. It is preferable that the vegetable dyeing material is used after it is extracted in boiled water for 2 hours or more.

The mordant functions to adsorb the natural coloring matter on cellulose. This mordant is formed of a metal salt that contains metal and an add, and if the coloring matter and the mordant meet each other, the metal of the mordant is combined with the coloring matter to ensure the color and improve the fastness. As the mordant, an iron mordant such as ferrous sulfate ($Fe_2SO_4.7H_2O$), ferrous chloride ($FeCl_2.H_2O$), iron nitrate ($Fe(NO_3)_2$, $Fe(NO_3)_3$), iron acetate ($Fe(CH_3COO)_2.4H_2O$) and the like; a copper mordant such as copper sulfate ($CuSO_4.5H_2O$), copper acetate ($Cu(CH_3COO)_2.H_2O$) and the like; an aluminium mordant such as aluminium sulfate ($Al_2(SO_4)_3.18H_2O$), aluminium acetate ($Al(CH_3COO)_3$), aluminium chloride ($AlCl_3.6H_2O$) and the like; a tin mordant such as sodium stannate ($Na_2SnO_5.3H_2O$) and the like; a zinc mordant such as zinc sulfate ($ZnSO_4$) and the like; a chrome mordant such as potassium dichromate ($K_2Cr_2O_7$), chrome acetate ($Cr(CH_3COO)_2$), chrome nitrate ($Cr(NO_3)_3.9H_2O$) and the like; an alkali mordant such as potassium carbonate and the like ($K_2CO_3$) and the like may be used.

A dyeing auxiliary agent may be auxiliarily used while the mordant is used if necessary. As the dyeing auxiliary agent, potassium hydrogen tartrate, an oxalic add, a tannic add, an acetic add, a formic add, ammonia, a citric add and the like may be used.

In addition, if necessary, the composition for cosmetic raw material that contains the cellulose dyed with the natural coloring matter according to the present invention may further comprise an antioxidant or a stabilizer. It is preferable that the antioxidant is one or more that are selected from the group consisting of butylated hydroxyanisole (BHA), butylated hydroxytoluene (BHT), tocopherol, an ascorbic acid, and beta-carotene.

A method for producing a composition for cosmetic raw material that contains the cellulose dyed with the natural coloring matter according to the present invention may comprise the steps of 1) extracting the natural coloring matter contained in the dyeing material by providing water in an amount of 5 to 30 times as much as the vegetable dyeing material and heating the vegetable dyeing material; 2) providing the microcrystalline cellulose to the extract solution that is obtained in step 1 to perform suspension; 3) providing a mordant to the suspension solution obtained in step 2 to perform mordancy; and 4) after the mordancy is finished, performing centrifugal separation, washing, and spray drying.

In the case of the vegetable dyeing material that mostly contains cellulose as a constitution material, step 2 may be omitted.

The particle size of the composition for cosmetic raw material that is produced by the method of the present invention is in the range of 0.001 to 30 µm, preferably 0.001 to 20 µm, and more preferably 0.001 to 10 µm. In the case of when the particle size of the composition for cosmetic raw material is more than 30 µm, when cosmetic products containing this are used in the skin of the user, the user may feel the sense of impurity.

In addition, the present invention can produce a visual carrier system that comprises the composition for cosmetic raw material containing cellulose dyed with the produced natural coloring matter, in detail, the visual carrier system that comprises 10 to 20% by weight of sucrose, 10 to 30% by weight of microcrystalline cellulose, 3 to 5% by weight of the composition for cosmetic raw material containing cellulose dyed with the natural coloring matter, 20 to 50% by weight of lactose, 20 to 25% by weight of corn starch, 1 to 5% by weight of shellac and 1 to 5% by weight of gelatinized corn starch on the basis of the total weight of the visual carrier system.

First, the gelatinized corn starch as a binder is put in water and agitated well, and then the microcrystalline cellulose and the composition for cosmetic raw material containing cellulose dyed with the natural coloring matter, lactose, and corn starch are added thereto and agitated well to produce the coating solution. After sucrose having the 40 to 50 meshes is used as a nucleus and added to a fluidized bed roto chamber, the produced coating solution is subjected to the powder layering in respects to the sucrose nucleus slowly and the rotor chamber is rotated. If the desired particle size of the visual carrier system is obtained, finally, the shellac is coated on the surface of the particle to control the final particle size of the visual carrier system to 20 to 30 meshes.

In the composition for cosmetic raw material and the visual carrier system comprising the same according to the present invention, by not using iron oxide chemical coloring matter and applying a typical and natural dyeing method of cloths to the microcrystalline cellulose that is the cosmetic raw material, the photostability that is a problem of the natural coloring matter in the related art is largely improved. In addition, in the composition for cosmetic raw material and the visual carrier system comprising the same according to the present invention, the tone of color is dull and different colors are smoothly mixed to show various colors, since the powder that is extracted from the natural plant and dried is used as the coloring matter, in the dyeing process, as a result, water pollution is reduced, which is environmentally friendly. Accordingly, the composition for cosmetic raw material and the visual carrier system comprising the same according to the present invention may be used instead of the natural coloring matter, and applied to cosmetics, and household supplies used in the skin of human.

MODE FOR THE INVENTION

A better understanding of the present invention may be obtained in light of the following Examples. However, the following Examples are set forth to illustrate but are not to be construed to limit the present invention.

EXAMPLE 1

Figure 1:
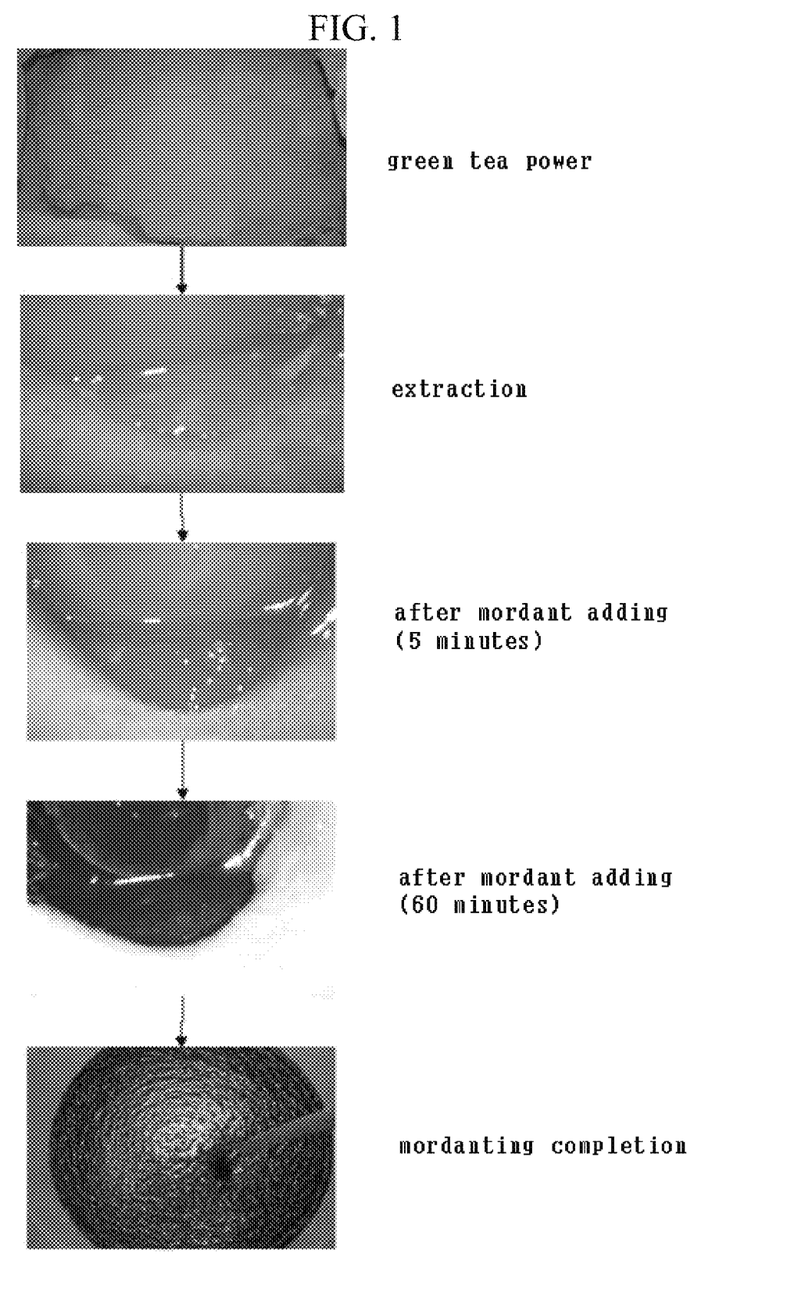
FIG. 1 is a view that illustrates a dyeing process of a composition for cosmetic raw material that contains green tea-dyed cellulose according to an embodiment of the present invention.
Figure 2:
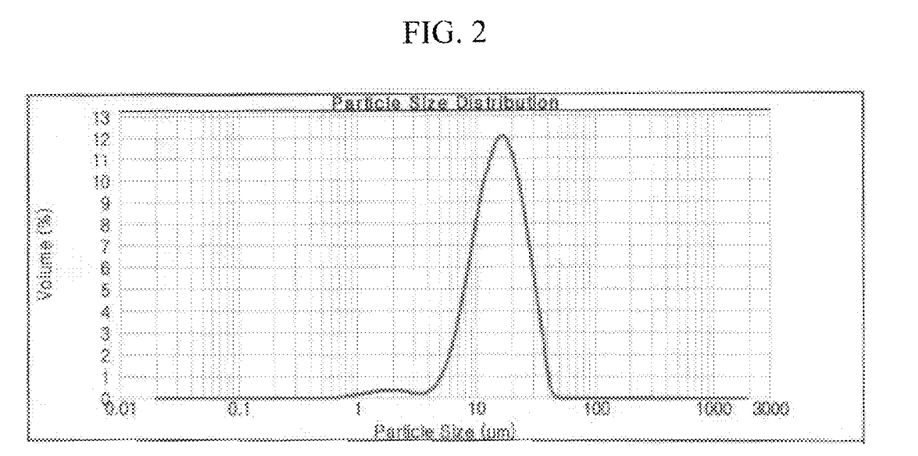
FIG. 2 is a view that illustrates an average particle size of a composition for cosmetic raw material that contains green tea-dyed cellulose according to an embodiment of the present invention.

Production of the Composition for Cosmetic Raw Material that Contained Cellulose Dyed with the Green Tea Powder Since the constitutional material of the fine powder green tea contained mostly cellulose, the cellulose was not separately used. After 30 kg of the fine powder green tea having the average particle size of not more than 7 μm was dispersed in 150 kg of purified water, it was added to the fermentation chamber and extracted at 90° C. for 2 hours at a rate of 200 rpm while oxygen was supplied at a rate of 250 L/min to extract the tanin component from the fine powder green tea. 500 g of iron sulfate ($FeSO_4$) that was the iron mordant was dissolved in 3 l of hot water and added to the fermentizing device. After the mordant was added and left for 1 hour, it was confirmed that the color was changed from green to black. After the mordanting was finished, the centrifugal separation was performed, the precipitated green tea-dyed cellulose was washed with purified water having the volume that was 20 to 30 times as much as the cellulose three times, the drying was performed under the condition of a drying temperature of 199° C. and the spray screen rate of 350 rpm by using the spray drier to produce the composition for cosmetic raw material that had the powder form and contained the green tea-dyed cellulose. The average particle size of the produced composition for cosmetic raw material that contained the green tea-dyed cellulose was measured and it was confirmed that the average particle size was about 16.83 μm, and this was shown in FIG. 2.

EXAMPLE 2

Production of the Composition for Cosmetic Raw Material that Contained Cellulose Dyed with the Gromwell Powder After 5 kg of the gromwell was dispersed in 150 kg of purified water, it was added to the fermentation chamber and extracted at 90° C. for 2 hours at a rate of 200 rpm while oxygen was supplied at a rate of 250 L/min to extract the coloring matter component from the gromwell. After 30 kg of the microcrystalline cellulose was dispersed in the extract solution, it was added to the fermentation chamber and agitated at 90° C. for 1 hours at a rate of 200 rpm while oxygen was supplied at a rate of 250 L/min to extract the coloring matter component from the gromwell. 200 g of zinc sulfate ($ZnSO_4$) that was the zinc mordant was dissolved in 2 l of hot water and added to the fermentizing device. After the mordant was added and left for 1 hour, it was confirmed that the color was changed to violet. After mordanting was finished, the centrifugal separation was performed, the precipitated gromwell-dyed cellulose was washed with purified water having a volume that was 20 to 30 times as much as the cellulose three times, the drying was performed under the condition of the drying temperature of 199° C. and the spray screen rate of 350 rpm by using the spray drier to produce the composition for cosmetic raw material that had the powder form and contained the gromwell-dyed cellulose.

EXAMPLE 3

Production of the Composition for Cosmetic Raw Material that Contained Cellulose Dyed with the Tumeric Powder The same method as Example 2 was performed to produce the composition for cosmetic raw material containing the tumeric-dyed cellulose, except that tumeric was used instead of the gromwell in Example 2. After the mordant was added and left for 1 hour, it was confirmed that the color was changed to yellow.

EXAMPLE 4

Production of the Composition for Cosmetic Raw Material that Contained Cellulose Dyed with the Safflower Powder The same method as Example 2 was performed to produce the composition for cosmetic raw material containing the safflower-dyed cellulose, except that the safflower was used instead of the gromwell in Example 2. After the mordant was added and left for 1 hour, it was confirmed that the color was changed to pink.

EXAMPLE 5

Production of the Visual Carrier System that Comprised the Composition for Cosmetic Raw Material Containing the Green Tea-Dyed Cellulose 50 g of the gelatinized corn starch as a binder was put in 1 l of water and well agitated to prepare the 5% solution, and 200 g of the microcrystalline cellulose, 30 g of the composition for cosmetic raw material that contained the green tea-dyed cellulose produced in Example 1, 300 g of lactose, and 250 g of corn starch were put therein and well agitated to produce the coating solution.

Figure 3:
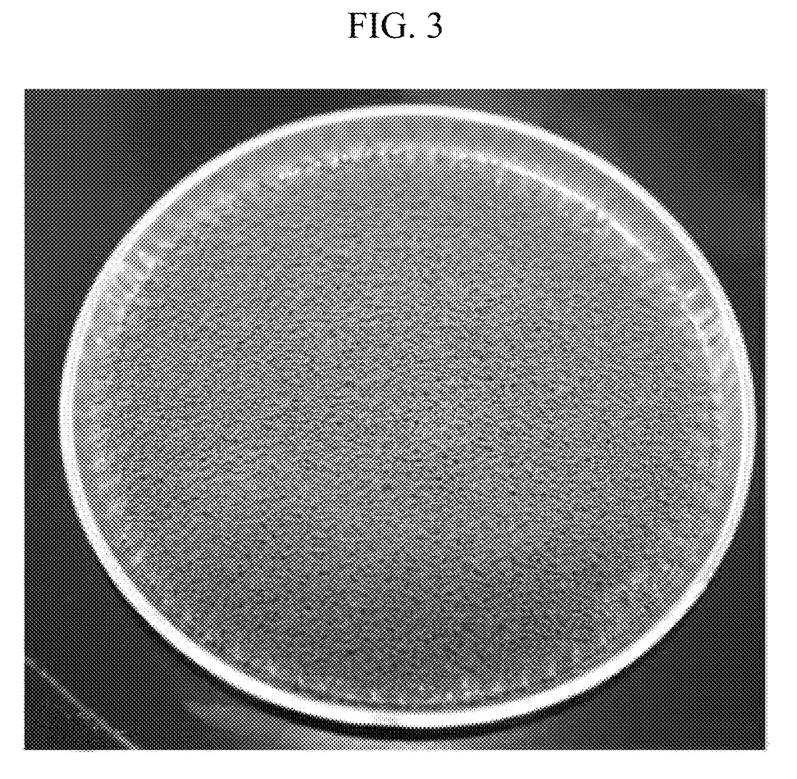
FIG. 3 is a view that illustrates a color difference meter measurement result of a visual carrier system that comprises a composition for cosmetic raw material containing green tea-dyed cellulose according to an embodiment of the present invention.

After 150 g of sucrose having 40 to 50 meshes was used as a nucleus and added to the fluidized bed rotor chamber, the produced coating solution was slowly powder-layered on the sucrose nucleus and the rotor chamber was rotated. If the desired particle size of the visual carrier system was obtained, finally, 20 g of the shellac was dissolved in 200 g of ethanol to prepare the 10% solution and the surface of the particle was coated with the solution. At this time, the final particle size of the visual carrier system was in the range of 20 to 30 meshes, and control of the size was performed by using various methods. The color of the produced visual carrier system that comprised the composition for cosmetic raw material containing green tea-dyed cellulose was measured by using the CR-300 (Minolta, USA) that was the tri-stimulus type portable color difference meter according to the CIELAB (L*a*b*) method authorized by Commission Internationale de l'Eclairage (CIE). The results are described in FIG. 3.

EXAMPLE 6

Figure 4:
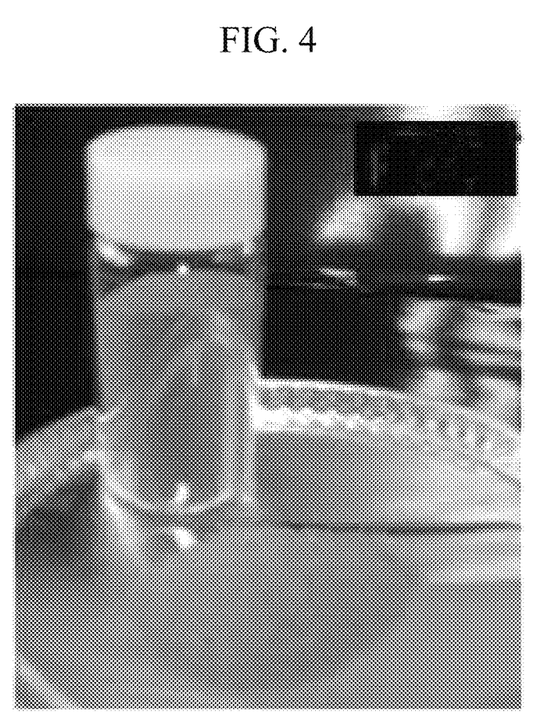
FIG. 4 is a view that illustrates a color difference meter measurement result of a visual carrier system that comprises a composition for cosmetic raw material containing gromwell-dyed cellulose according to an embodiment of the present invention.

Production of the Visual Carrier System that Comprised the Composition for Cosmetic Raw Material Containing the Gromwell-Dyed Cellulose The same method as Example 5 was performed to produce the visual carrier system that comprised the composition for cosmetic raw material containing the gromwell-dyed cellulose, except that the composition for cosmetic raw material containing the gromwell-dyed cellulose produced in Example 2 was used instead of the composition for cosmetic raw material containing the green tea-dyed cellulose in Example 5. The color difference meter measurement results of the produced visual carrier system are shown in FIG. 4.

EXAMPLE 7

Figure 5:
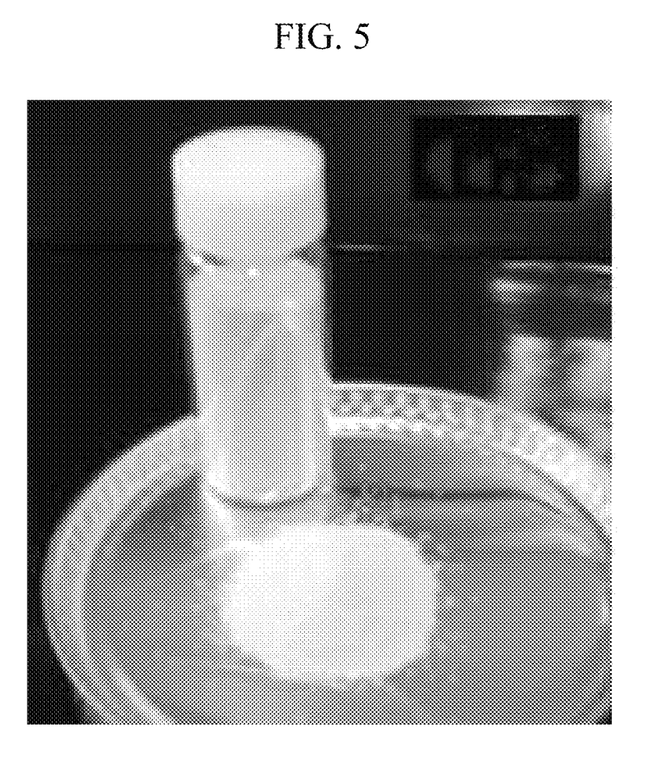
FIG. 5 is a view that illustrates a color difference meter measurement result of a visual carrier system that comprises a composition for cosmetic raw material containing tumeric-dyed cellulose according to an embodiment of the present invention.

Production of the Visual Carrier System that Comprised the Composition for Cosmetic Raw Material Containing the Tumeric-Dyed Cellulose The same method as Example 5 was performed to produce the visual carrier system that comprised the composition for cosmetic raw material containing the tumeric-dyed cellulose, except that the composition for cosmetic raw material containing the tumeric-dyed cellulose produced in Example 3 was used instead of the composition for cosmetic raw material containing the green tea-dyed cellulose in Example 5. The color difference meter measurement results of the produced visual carrier system are shown in FIG. 5.

EXAMPLE 8

Figure 6:
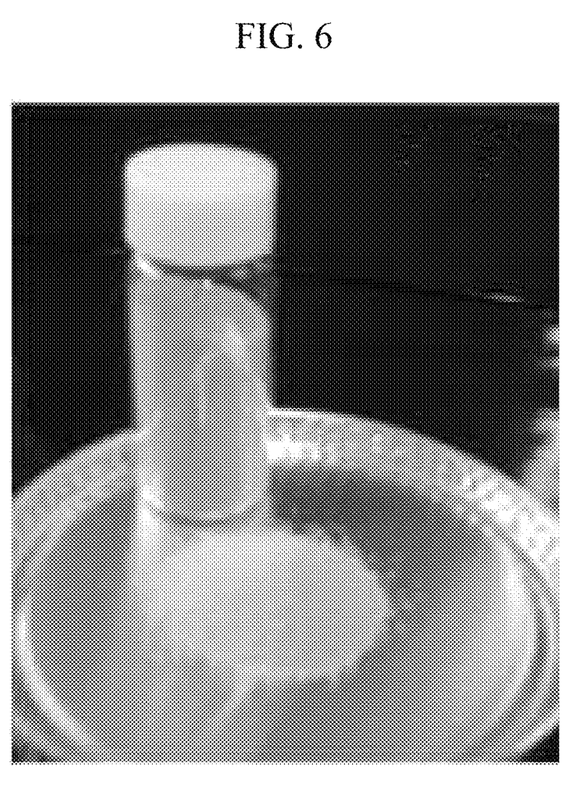
FIG. 6 is a view that illustrates a color difference meter measurement result of a visual carrier system that comprises a composition for cosmetic raw material containing safflower-dyed cellulose according to an embodiment of the present invention.

Production of the Visual Carrier System that Comprised the Composition for Cosmetic Raw Material Containing the Safflower-Dyed Cellulose The same method as Example 5 was performed to produce the visual carrier system that comprised the composition for cosmetic raw material containing the safflower-dyed cellulose, except that the composition for cosmetic raw material containing the safflower-dyed cellulose produced in Example 4 was used instead of the composition for cosmetic raw material containing the green tea-dyed cellulose in Example 5. The color difference meter measurement results of the produced visual carrier system are shown in FIG. 6.

COMPARATIVE EXAMPLE 1

Production of the Gromwell Coloring Matter to which the Typical and Natural Dyeing Method was not Applied After 5 kg of the gromwell was dispersed in 150 kg of purified water, it was heated for 2 hours and extracted to extract the coloring matter component. After the extract solution was filtered, the extract was concentrated and dried by using the spray drier under the condition of the drying temperature of 199° C. and the spray screen rate of 350 rpm to obtain the gromwell coloring matter of powder form.

COMPARATIVE EXAMPLE 2

Production of the Tumeric Coloring Matter to which the Typical and Natural Dyeing Method was not Applied The same method as Comparative Example 1 was performed to obtain tumeric coloring matter of powder form, except that the tumeric coloring matter was used instead of the gromwell in Comparative Example 1.

COMPARATIVE EXAMPLE 3

Production of the Safflower Coloring Matter to which the Typical and Natural Dyeing Method was not Applied The same method as Comparative Example 1 was performed to obtain safflower coloring matter of powder form, except that the safflower coloring matter was used instead of the gromwell in Comparative Example 1.

EXPERIMENTAL EXAMPLE 1

Photostability Test of the Composition for Cosmetic Raw Material According to the Present Invention In order to confirm photostability of the composition for cosmetic raw material according to the present invention, the following test was performed.

1. High Temperature Stability Test

The compositions for cosmetic raw material that were produced in Examples 1 to 4, and Comparative Examples 2 and 3 were left at 45° C., and the discoloring thereof was observed after 60 days, 90 days, 120 days, and 150 days. The evaluation standard was obtained by measuring the degree of discoloration by the eye, and the degree of discoloration was evaluated in the range of 0 to −5 (0: no change, −1: very little pale, −2: slightly pale, −3: pale, −4: slightly discolored, and −5: very discolored).

The results are described in Table 1.

TABLE 1

| | Example | | | | Comparative Example | |
|---|---|---|---|---|---|---|
| | 1 (green tea) | 2 (gromwell) | 3 (tumeric) | 4 (safflower) | 2 (tumeric) | 3 (safflower) |
| after 60 days | 0 | 0 | 0 | 0 | −1 | −4 |
| after 90 days | 0 | 0 | 0 | 0 | −2 | −4 |
| after 120 days | 0 | 0 | 0 | 0 | −3 | −4 |
| after 150 days | 0 | 0 | 0 | 0 | −3 | −4 |

As shown in Table 1, it was confirmed that the composition for cosmetic raw material containing cellulose dyed with the natural coloring matter according to the present invention was not discolored even though it was left at a high temperature (45° C.) for not less than 150 days, but the cosmetic composition containing the natural coloring matter to which the typical and natural dyeing method was not applied was discolored. Therefore, it can be seen that the composition for cosmetic raw material according to the present invention have excellent high temperature stability as compared to a general natural coloring matter.

2. Fluorescence Stability Test

The compositions for cosmetic raw material that were produced in Examples 1 to 4, and Comparative Examples 1 and 2 were left under the fluorescent lamp, and the discoloring thereof was observed after 60 days, 90 days, 120 days, and 150 days. The evaluation standard was obtained by measuring the degree of discoloration by the eye, and the degree of discoloration was evaluated in the range of 0 to −5 (0: no change, −1: very little pale, −2: slightly pale, −3: pale, −4: slightly discolored, and −5: very discolored).

The results are described in Table 2.

TABLE 2

|  | Example | | | | Comparative Example | |
|---|---|---|---|---|---|---|
|  | 1 (green tea) | 2 (gromwell) | 3 (tumeric) | 4 (safflower) | 1 (gromwell) | 2 (tumeric) |
| after 60 days | 0 | 0 | 0 | 0 | −1 | −1 |
| after 90 days | 0 | 0 | 0 | 0 | −2 | −2 |
| after 120 days | 0 | 0 | 0 | 0 | −2 | −2 |
| after 150 days | 0 | 0 | 0 | 0 | −2 | −3 |

As shown in Table 2, it was confirmed that the composition for cosmetic raw material containing cellulose dyed with the natural coloring matter according to the present invention was not discolored even though it was left under the fluorescent lamp for not less than 150 days, but the cosmetic composition containing the natural coloring matter to which the typical and natural dyeing method was not applied became slightly pale. Therefore, it can be seen that the composition for cosmetic raw material according to the present invention have excellent fluorescence stability as compared to a general natural coloring matter.

3. Sunlight Stability Test

The compositions for cosmetic raw material that were produced in Examples 1 to 4, and Comparative Example 2 were left on the roof, which was in the sun, and the discoloring thereof was observed after 1 day, 3 days, and 5 days. The evaluation standard was obtained by measuring the degree of discoloration by the eye, and the degree of discoloration was evaluated in the range of 0 to −5 (0: no change, −1: very little pale, −2: slightly pale, −3: pale, −4: slightly discolored, and −5: very discolored).

The results are described in Table 3.

TABLE 3

|  | Example | | | | Comparative Example 2 (tumeric) |
|---|---|---|---|---|---|
|  | 1 (green tea) | 2 (gromwell) | 3 (tumeric) | 4 (safflower) | |
| after 1 day | 0 | 0 | 0 | 0 | −1 |
| after 3 days | 0 | 0 | 0 | 0 | −3 |
| after 5 days | 0 | 0 | 0 | 0 | −4 |

As shown in Table 3, it was confirmed that the composition for cosmetic raw material containing cellulose dyed with the natural coloring matter according to the present invention was not discolored even though it was left under the sunlight for not less than 5 days, but the cosmetic composition containing the natural coloring matter to which the typical and natural dyeing method was not applied was discolored. Therefore, it can be seen that the composition for cosmetic raw material according to the present invention have excellent sunlight stability as compared to a general natural coloring matter.

As a result, it can be seen that in the composition for cosmetic raw material containing cellulose dyed with the natural coloring matter according to the present invention, high temperature stability, fluorescence stability, and sunlight stability are excellent as compared to the cosmetic composition containing the natural coloring matter to which the typical and natural dyeing method is not applied.

Industrial Applicability

In the composition for cosmetic raw material containing cellulose dyed with the natural coloring matter and the visual carrier system comprising the same according to the present invention, by using no iron oxide chemical coloring matter and applying a typical and natural dyeing method of cloths to the microcrystalline cellulose that is the cosmetic raw material, photostability that is a problem of the natural coloring matter in the related art is largely improved. In addition, in the composition for cosmetic raw material and the visual carrier system comprising the same according to the present invention, the tone of color is dull and different colors are smoothly mixed to show various colors, since the powder that is extracted from the natural plant and dried is used as the coloring matter, in the dyeing process, water pollution is reduced, which is environmentally friendly. Accordingly, the composition for cosmetic raw material and the visual carrier system comprising the same according to the present invention may be used instead of the natural coloring matter, and applied to cosmetics, and household supplies used on the skin of a human.

The invention claimed is:

1. A composition for cosmetic raw material, comprising:
a nucleus consisting of sucrose on which a coating solution is powder-layered, the coating solution comprising;
   cellulose dyed with a natural coloring matter, comprised of:
      0.1 to 99.0 parts by weight of micro-crystalline cellulose on the basis of 100 parts by weight of the total weight of the cellulose dyed with the natural coloring matter;
      0.10 to 20.0 parts by weight of a vegetable dyeing material on the basis of 100 parts by weight of the total weight of the cellulose dyed with the natural coloring matter, the vegetable dyeing material selected from the group consisting of a green tea, a *Caesalpiniae lignum*, safflower, a gromwell, and an indigo plant; and
      0.01 to 10.0 parts by weight of a mordant on the basis of 100 parts by weight of the total weight of the cellulose dyed with the natural coloring matter;
lactose;
corn starch;
micro-crystalline cellulose; and
gelatinized corn starch;
shellac coated on the sucrose nucleus on which the coating solution is powder-layered; and
wherein said cellulose dyed with the natural coloring matter has a particle size in the range of 0.001 to 30 μm; and
wherein said composition is added to a cosmetic formulation.

2. The composition for cosmetic raw material according to claim 1, wherein the microcrystalline cellulose is selected from the microcrystalline cellulose itself or a dried powder obtained by extracting the vegetable dyeing material.

3. The composition for cosmetic raw material according to claim 1, wherein the mordant comprises one selected from the group consisting of an iron mordant, a copper mordant, an aluminium mordant, a tin mordant, a zinc mordant, a chrome mordant, and an alkali mordant.

4. The composition for cosmetic raw material according to claim 1, wherein the composition further comprises a dyeing auxiliary agent, an antioxidant, a stabilizer, or a combination thereof.

5. The composition for cosmetic raw material according to claim 4, wherein the composition comprises the dyeing auxiliary agent selected from the group consisting of potassium hydrogen tartrate, oxalic acid, tannic acid, acetic acid, formic acid, ammonia, citric acid, and a combination thereof.

6. The composition for cosmetic raw material according to claim 4, wherein the composition comprises the antioxidant selected from the group consisting of butylated hydroxyanisole (BRA), butylated hydroxytoluene (BRT), tocopherol, ascorbic acid, beta-carotene, and a combination thereof.

7. A visual carrier system that comprises the composition for cosmetic raw material containing cellulose dyed with the natural coloring matter according to claim 1.

8. A visual carrier system that comprises the composition for cosmetic raw material containing cellulose dyed with the natural coloring matter according to claim 2.

9. A visual carrier system that comprises the composition for cosmetic raw material containing cellulose dyed with the natural coloring matter according to claim 3.

10. A visual carrier system that comprises the composition for cosmetic raw material containing cellulose dyed with the natural coloring matter according to claim 4.

11. A visual carrier system that comprises the composition for cosmetic raw material containing cellulose dyed with the natural coloring matter according to claim 5.

12. A visual carrier system that comprises the composition for cosmetic raw material containing cellulose dyed with the natural coloring matter according to claim 6.

13. The composition of claim 1, wherein the composition comprises the vegetable dyeing material of the green tea.

14. The composition of claim 1, wherein the composition comprises the vegetable dyeing material of the *Caesalpiniae lignum*.

15. The composition of claim 1, wherein the composition comprises the vegetable dyeing material of the safflower.

16. The composition of claim 1, wherein the composition comprises the vegetable dyeing material of the gromwell.

17. The composition of claim 1, wherein the microcrystalline cellulose comprises a dried powder obtained by extracting the vegetable dyeing material.

* * * * *